(12) United States Patent
Bao et al.

(10) Patent No.: US 9,880,121 B2
(45) Date of Patent: Jan. 30, 2018

(54) BIOELECTRONIC BINDING ASSAY USING PEAK PROFILING

(71) Applicant: OHMX Corporation, Evanston, IL (US)

(72) Inventors: Yijia Paul Bao, Deer Park, IL (US); Adam G. Gaustad, Kansas City, MO (US); Dimitra Georganopoulou, Lincolnwood, IL (US); Fang Lai, Deer Park, IL (US); Rebecca Hoo, Palatine, IL (US)

(73) Assignee: OHMX Corporation, Evanston, IL (US)

( * ) Notice: Subject to any disclaimer, the term of this patent is extended or adjusted under 35 U.S.C. 154(b) by 341 days.

(21) Appl. No.: 14/700,062

(22) Filed: Apr. 29, 2015

(65) Prior Publication Data

US 2015/0323484 A1   Nov. 12, 2015

Related U.S. Application Data

(60) Provisional application No. 61/985,969, filed on Apr. 29, 2014, provisional application No. 61/985,976, filed on Apr. 29, 2014.

(51) Int. Cl.
*G01N 27/26* (2006.01)
*G01N 33/543* (2006.01)

(52) U.S. Cl.
CPC ......... *G01N 27/26* (2013.01); *G01N 33/5438* (2013.01)

(58) Field of Classification Search
CPC ............................ G01N 27/26; G01N 33/5438
See application file for complete search history.

(56) References Cited

U.S. PATENT DOCUMENTS

2012/0027310 A1   2/2012   Lukas et al.
2014/0027310 A1   1/2014   Gaustad et al.

OTHER PUBLICATIONS

U.S. Appl. No. 14/281,865, filed May 19, 2014, Bertin et al.
U.S. Appl. No. 14/254,817, filed Apr. 16, 2014, Ahrens et al.
U.S. Appl. No. 13/793,752, filed Mar. 11, 2013, Bertin.
U.S. Appl. No. 13/667,713, filed Nov. 2, 2012, Bertin.
U.S. Appl. No. 13/068,938, filed May 23, 2011, Ahrens et al.
U.S. Appl. No. 13/798,461, filed Mar. 13, 2013, Ahrens et al.

(Continued)

*Primary Examiner* — J. Christopher Ball
(74) *Attorney, Agent, or Firm* — Wolf, Greenfield & Sacks, P.C.

(57) ABSTRACT

In one aspect, a method for detection of a target in a sample based on the change of electrochemical cyclic voltammetry peak profile is provided. The method may involve at least two or more electroactive moieties (EAMs) comprising a transitional metal complex and an anchor group. Said transitional metal complex may be capable of reversibly or semi-reversibly transferring one or more electrons. Said anchor group may allow said EAMs to covalently attach to a solid support, forming a self-assembled monolayer (SAM) on the surface. At least one EAM may further comprises a capture ligand that can be recognized and bound by a target or a surrogate target. When a sample is introduced to an EAM, the interaction between said capture ligand and said target or surrogate target may lead to change of the properties of the SAM containing all EAMs involved. Said change can be detected by an electrochemical detection system.

25 Claims, 9 Drawing Sheets

(56) References Cited

OTHER PUBLICATIONS

U.S. Appl. No. 14/593,318, filed Jan. 9, 2015, Ahrens et al.
U.S. Appl. No. 14/033,169, filed Sep. 20, 2013, Ahrens et al.
U.S. Appl. No. 13/952,345, filed Jul. 26, 2013, Gaustad et al.
U.S. Appl. No. 13/354,200, filed Jan. 19, 2012, Bertin et al.
U.S. Appl. No. 13/653,931, filed Oct. 17, 2012, Gaustad et al.
U.S. Appl. No. 13/737,634, filed Jan. 9, 2013, Bertin et al.
U.S. Appl. No. 13/952,215, filed Jul. 26, 2013, Bao et al.
International Search Report and Written Opinion dated Jul. 3, 2015 for Application No. PCT/US2015/028316.

BIOELECTRONIC BINDING ASSAY USING PEAK PROFILING

RELATED APPLICATIONS

This application claims priority under 35 U.S.C. §119(e) to US provisional patent applications, U.S. Ser. No. 61/985,969, filed Apr. 29, 2014, entitled "Bioelectronic Binding Assay Using Peak Profiling" and U.S. Ser. No. 61/985,976, filed Apr. 29, 2014, entitled "Bioelectronic Binding Assay on Pre-formed SAMS Using Peak Profiling," the contents of each of which are incorporated herein by reference in their entirety.

FIELD OF THE INVENTION

Methods for bioelectronic binding assays to detect a target analyte in a sample are generally described.

BACKGROUND OF THE INVENTION

Electron transfer reactions are critical steps in a wide variety of biological interactions ranging from photosynthesis to aerobic respiration. Studies of electron transfer reactions in both chemical and biological systems have yielded a large body of knowledge and a strong theoretical base, which describes the rate of electron transfer in terms of a small number of parameters.

With this knowledge, an electroactive moiety (EAM) may be designed as a sensing molecule. The magnitude of electron transfer is changed upon its interaction with a target.

SUMMARY OF THE INVENTION

It is the object of one embodiment of the present invention to provide a method, termed bioelectronic binding assay, for detecting a target, either directly or via a surrogate target, using two or more EAMs.

In one aspect, the present invention describes a method by which a target of interest in a sample is detected using electroactive moieties (EAMs) self-assembled to form a monolayer on an electrode. When multiple species of EAMs are involved, each EAM species may have a specific structure and/or a specific electrochemical (E-chem) cyclic voltammetry peak profile (CVPP) $E^0$. Different EAMs may be distinguished by assigning a number to correlate a distinct EAM with its associated $E^0$. For example, EAM1 and EAM2 have different E-chem CVPP $E_1^0$ and $E_2^0$, respectively. In some embodiments, only two types of EAM are used to form a self-assembled monolayer (SAM) on an electrode. In some such embodiments, one EAM, EAM1 having $E_1^0$, has a capture ligand that specifically binds a target of interest or a surrogate target. The other EAM, EAM2 having $E_2^0$ may not have a capture ligand. When a sample containing said target of interest is introduced to said EAMs, said binding ligand of said EAM1 is bound to its specific target or surrogate target whereas said EAM2 is not bound.

In some embodiments, a sample is added directly to a solution comprising an EAM mix comprising two EAMs, EAM1 and EAM2, mixed at a known ratio, wherein EAM1 further comprises a binding ligand capable of binding to a target of interest, to form an assay mix. If no target is present, EAM1 and EAM2 may form a self-assembled monolayer (SAM) when introduced to an electrode with a particular known ratio of the magnitude of $E_1^0$ and $E_2^0$. If said target of interest is present in said sample, said binding ligand of EAM1 may bind to said target. When bound to said target, said EAM1 is sterically hindered from forming a self-assembled monolayer (SAM). Said assay mix is then contacted with an electrode. When in contact with said electrode, remaining free EAM1 and EAM2 in said assay mix may self-assemble into a monolayer while the bound EAM1 is hindered from doing so. The ratio of EAM1 and EAM2 in the monolayer varies depending on the amount of EAM1 sterically hindered from forming a SAM due to binding of said target. The magnitude of $E_1^0$ and $E_2^0$ is changed accordingly and is proportional to the amount of target present in said sample.

In some embodiments, a sample is added to a solution for a sandwich immunoassay as further described below, through which a sandwich is formed with the target of interest that is additionally linked to a binding partner. Said binding partner becomes a surrogate target. In some embodiments, an additional washing step may be performed. After removal of unbound surrogate target, the sandwich (containing said linked surrogate target) may be added directly to a solution comprising an EAM mix comprising EAM1 and EAM2, mixed at a known ratio, wherein EAM1 further comprises a binding ligand capable of binding to said surrogate target, to form an assay mix. Said binding ligand of EAM1 may bind to said surrogate target associated with said sandwich; thereby bound EAM1 is sterically hindered from forming a self-assembled monolayer (SAM). When said assay mix is contacted with an electrode, remaining free EAM1 and EAM2 may self-assemble to form a monolayer. The ratio of EAM1 and EAM2 in the monolayer varies depending on the amount of EAM1 sterically hindered from forming a SAM due to the binding of said surrogate target associated with said sandwich. The magnitude of $E_1^0$ and $E_2^0$ is changed accordingly and is proportional to the amount of target present in said sample.

In some embodiments, a sample is added to a solution for a sandwich immunoassay as further described below, through which a sandwich is formed with the target of interest that is additionally linked to a binding partner. In some instances, after removal of the sandwich, the remaining free binding partners left in solution become a surrogate target that is inversely proportional to the concentration of target of interest present in said sample. The solution containing surrogate targets may be added directly to a solution comprising an EAM mix comprising two EAMs, EAM1 and EAM2, mixed at a known ratio, wherein EAM1 comprises a binding ligand capable of binding said surrogate target, to form an assay mix. Said binding ligand of EAM1 is bound with said surrogate target; thereby EAM1 is hindered from forming a self-assembled monolayer (SAM). Said assay mix is then contacted with an electrode, remaining free EAM1 and EAM2 are self-assembled into a monolayer. The ratio of EAM1 and EAM2 in the monolayer varies depending on the amount of EAM1 sterically hindered from forming a SAM due to the binding of said surrogate target in solution. The magnitude of $E_1^0$ and $E_2^0$ is changed accordingly and is proportional to the amount of surrogate target present in solution, which is in turn inversely proportional to the amount of target present in said sample.

In some embodiments, a target of interest in a sample is detected using preformed SAMs of EAM1 and EAM2 mixed at a known ratio. When a target binds to EAM1, said target changes reorganization energy around EAM1, resulting in $E_1^{t0}$. The change from $E_1^0$ to $E_1^{t0}$ and $E_1^{t0}$ relative to $E_2^0$ is proportional to the amount of target.

In another aspect, a method for detecting at least one target in a sample, said method comprising contacting a sample with an EAM mix comprising two or more electroactive moieties (EAMs) mixed at a known ratio, said EAMs possessing a distinct redox potential $E^0$ (e.g. $E_1^0$, $E_2^0$, $E_3^0$ ... ) and said EAMs comprising i. a transitional metal complex and ii. an anchor group, wherein at least one of said EAMs further comprises a capture ligand that can be recognized and bound by a target to form an assay mix, contacting said assay mix with an electrode under conditions wherein EAMs form a self-assembled monolayer (SAM), and detecting signal to determine electrochemical (E-chem) cyclic voltammetry peak profile (CVPP) as an indication of the presence of said target in said sample is provided.

In another aspect, a method for detecting at least one target in a sample, said method comprising contacting a sample with an EAM mix comprising two or more electroactive moiety species (EAMs) mixed at a known ratio, said EAMs possessing a distinct redox potential $E^0$ (e.g. $E_1^0$, $E_2^0$, $E_3^0$ ... ) and said EAMs comprising i. a transitional metal complex and ii. an anchor group, wherein at least one of said EAMs further comprises a capture ligand that can bind to said target to form an assay mix, contacting said assay mix with an electrode under conditions wherein EAMs form a self-assembled monolayer (SAM), and detecting signal to determine electrochemical (E-chem) cyclic voltammetry peak profile (CVPP) as an indication of the presence of said target in said sample is provided.

In another aspect, a method of detecting at least one target analyte in a sample, said method comprising contacting said sample with a first capture ligand comprising i. binding site specific for said target and ii. a solid support, a second capture ligand comprising i. a binding site specific for said target, being bound in a different location that said first capture ligand and ii. a tag capable of binding to a binding partner, and a binding partner capable of binding to said probe of said second capture ligand and an EAM as a surrogate target to form a sandwich, isolating said sandwich and separating it from unbound said binding partners (surrogate targets), contacting either said sandwich or said unbound binding partners with an EAM mix comprising two or more electroactive moiety species (EAMs) mixed at a known ratio, said EAMs possessing a distinct redox potential $E^0$ (e.g. $E_1^0$, $E_2^0$, $E_3^0$ ... ) and said EAMs comprising i. a transitional metal complex and ii. an anchor group, wherein at least one of said EAMs further comprises a capture ligand that can bind to said surrogate target to form an assay mix, contacting said assay mix with an electrode under conditions wherein EAMs form a self-assembled monolayer (SAM), and detecting signal to determine electrochemical (E-chem) cyclic voltammetry peak profile (CVPP) as an indication of the presence of said target in said sample is provided.

In another aspect, a method of detecting at least one target analyte in a sample, said method comprising providing a solid support comprising an electrode comprising a preformed self-assembled monolayer (SAM) comprising two or more electroactive moiety species (EAMs) mixed at a known ratio, said EAMs possessing a distinct redox potential $E^0$ (e.g. $E_1^0$, $E_2^0$, $E_3^0$ ... ) and said EAMs comprising i. a transitional metal complex and ii. an anchor group, wherein at least one of said EAMs further comprising a capture ligand that can bind said target, contacting said electrode with said sample, and detecting signal to determine electrochemical (E-chem) cyclic voltammetry peak profile (CVPP) as an indication of the presence of said target in said sample is provided.

In another aspect, a method of detecting at least one target analyte in a sample, said method comprising providing a solid support comprising an electrode comprising a preformed self-assembled monolayer (SAM) comprising two or more electroactive moiety species (EAMs) mixed at a known ratio, said EAMs possessing a distinct redox potential $E^0$ (e.g. $E_1^0$, $E_2^0$, $E_3^0$ ... ) and said EAMs comprising i. a transitional metal complex and ii. an anchor group, wherein at least one of said EAMs further comprises a capture ligand that can bind said target or a surrogate target, contacting said sample with a first capture ligand comprising i. a binding site specific for said target and ii. a solid support, a second capture ligand comprising i. a binding site specific for said target, being bound in a different location that said first capture ligand and ii. a tag capable of binding to a binding partner, and a binding partner capable of binding to said probe of said second capture ligand and an EAM as a surrogate target to form a sandwich, isolating said sandwich and separating it from unbound said binding partners (surrogate targets), contacting either said sandwich or said unbound binding partners with said electrode, and detecting signal to determine electrochemical (E-chem) cyclic voltammetry peak profile (CVPP) as an indication of the presence of said target in said sample.

In one embodiment of any one of the methods provided, said EAM mix comprises two EAMs, EAM1 and EAM2, in a solution, wherein EAM1 further comprises a capture ligand that can be bound by said target.

In another embodiment of any one of the methods provided, said target is directly bound to EAM1 through said capture ligand, sterically hindering said EAM1 from forming a SAM.

In another embodiment of any one of the methods provided, the ratio of EAM1 and EAM2 in a SAM is changed, resulting in change of CVPP ($E_1^0$ & $E_2^0$).

In another embodiment of any one of the methods provided, the change of CVPP is proportional to the amount of said target.

In another embodiment of any one of the methods provided, said target is bound between (i) a first capture molecule bound to a solid support and (ii) a second capture molecule comprising a probe bound to a binding partner, said binding partner being capable of binding to EAM1, serving as a surrogate target.

In another embodiment of any one of the methods provided, said target is bound between (i) a first capture molecule bound to a solid support and (ii) a second capture molecule with a probe bound with a binding partner and is removed. In one such embodiment, free form of said binding partner is capable of binding to EAM1, serving as a surrogate target.

In another embodiment of any one of the methods provided, a sample is introduced to a preformed SAM comprising EAM1 and EAM2.

In another embodiment of any one of the methods provided, a target is bound to EAM1, causing reorganization of energy; thereby resulting in change of $E_1^0$ to $E_1'^0$, which in turn changes CVPP ($E_1^0$, $E_1'^0$, and $E_2^0$).

In another embodiment of any one of the methods provided, said capture ligand or capture molecules are independently selected from the group consisting of monoclonal antibodies, fragments of monoclonal antibodies, polyclonal antibodies, fragments of polyclonal antibodies, proteins, peptides, aptamers, nucleic acids, or small molecules.

In another embodiment of any one of the methods provided, said transition metal complex includes a transition metal selected from the group consisting of iron, ruthenium and osmium.

In another embodiment of any one of the methods provided, said transition metal complex comprises a ferrocene and substituted ferrocene.

In another embodiment of any one of the methods provided, said anchor group comprises a sulfur, amine, silicon, pyridinyl or other group that interacts with an electrode.

In another embodiment of any one of the methods provided, two distinct EAM species are used, EAM1 with $E_1^0$ and EAM2 with $E_2^0$, wherein EAM1 further comprises said capture ligand that can be recognized and bound by a target of interest or surrogate target.

In another embodiment of any one of the methods provided, said target or said surrogate target is bound to EAM1 through said capture ligand, In another embodiment of any one of the methods provided, said target or surrogate target, if bound, sterically hinders said EAM1 from forming a SAM; altering the ratio of EAM1 and EAM2 in a SAM, resulting in change of CVPP ($E_1^0$ & $E_2^0$).

In another embodiment of any one of the methods provided, a target or surrogate target is bound to EAM1, causing reorganization of energy; thereby resulting in change of $E_1^0$ to $E_1^{'0}$, which in turn changes CVPP ($E_1^0$, $E_1^{'0}$, and $E_2^0$).

In another embodiment of any one of the methods provided, at least one washing step is performed as part of the sandwich isolation and separation process.

In another embodiment of any one of the methods provided, said change in CVPP is proportional to the amount of unbound surrogate target present in the mix, said amount of surrogate target being inversely proportional to the amount of said target in said sample.

In another aspect, a composition comprising an electrode comprising a self-assembled monolayer (SAM) comprising two or more electroactive moiety species (EAMs) mixed at a known ratio, said EAMs possessing a distinct redox potential $E^0$ (e.g. $E_1^0$, $E_2^0$, $E_3^0$ . . . ) and said EAMs comprising a transitional metal complex and an anchor group, wherein at least one of said EAMs further comprises a capture ligand that can be recognized and bound by a target of interest or surrogate target is provided.

In another aspect, a method for detecting at least one target in a sample that is any one of the methods provided herein such as in the examples is provided.

In another aspect, a method for producing a monolayer on an electrode that is any one of the methods provided herein above such as in the examples is provided.

In another aspect, a composition comprising a monolayer that is any one of the compositions provided herein such as in the examples is provided.

BRIEF DESCRIPTION OF THE FIGURES

FIG. 1A depicts self-assembled monolayer (SAM) formation when no target is present, according to certain embodiments. FIG. 1B depicts SAM formation when target is present, according to certain embodiments. Target in a sample directly interacting with EAM1 (binding EAM) in a solution. The EAM1 bound to target is sterically hindered from forming a SAM, resulting in a change of the ratio of EAM1 and EAM2 (standard EAM) in the SAM formed when target is present in said sample. The change is determined through peak profiling and is proportional to the amount of the target present in a sample.

FIG. 5A shows signal for EAM1 and EAM2 varying across target (e.g. streptavidin) concentrations. Increasing amount of the target binding to EAM1 results in varying signals that are directly proportional to the amount of the target. FIG. 5B shows the trend of peak ratio of EAM1 to EAM2 plotted against target concentration, illustrating the trend in this relationship.

DETAILED DESCRIPTION OF THE INVENTION

Figure 1A:
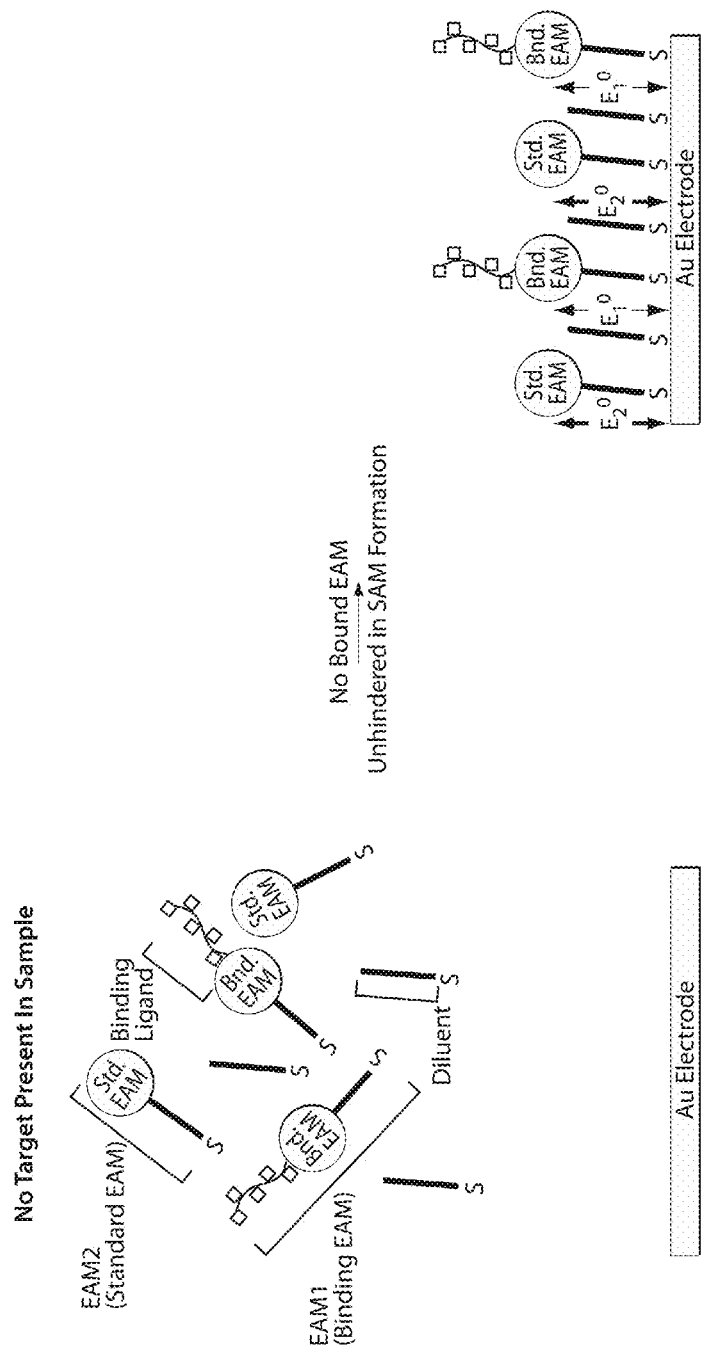
FIGS. 1A to 1B. A schematic describing a method for the bioelectronic binding assay in solution using peak profiling, according to one set of embodiments.
Figure 1B:
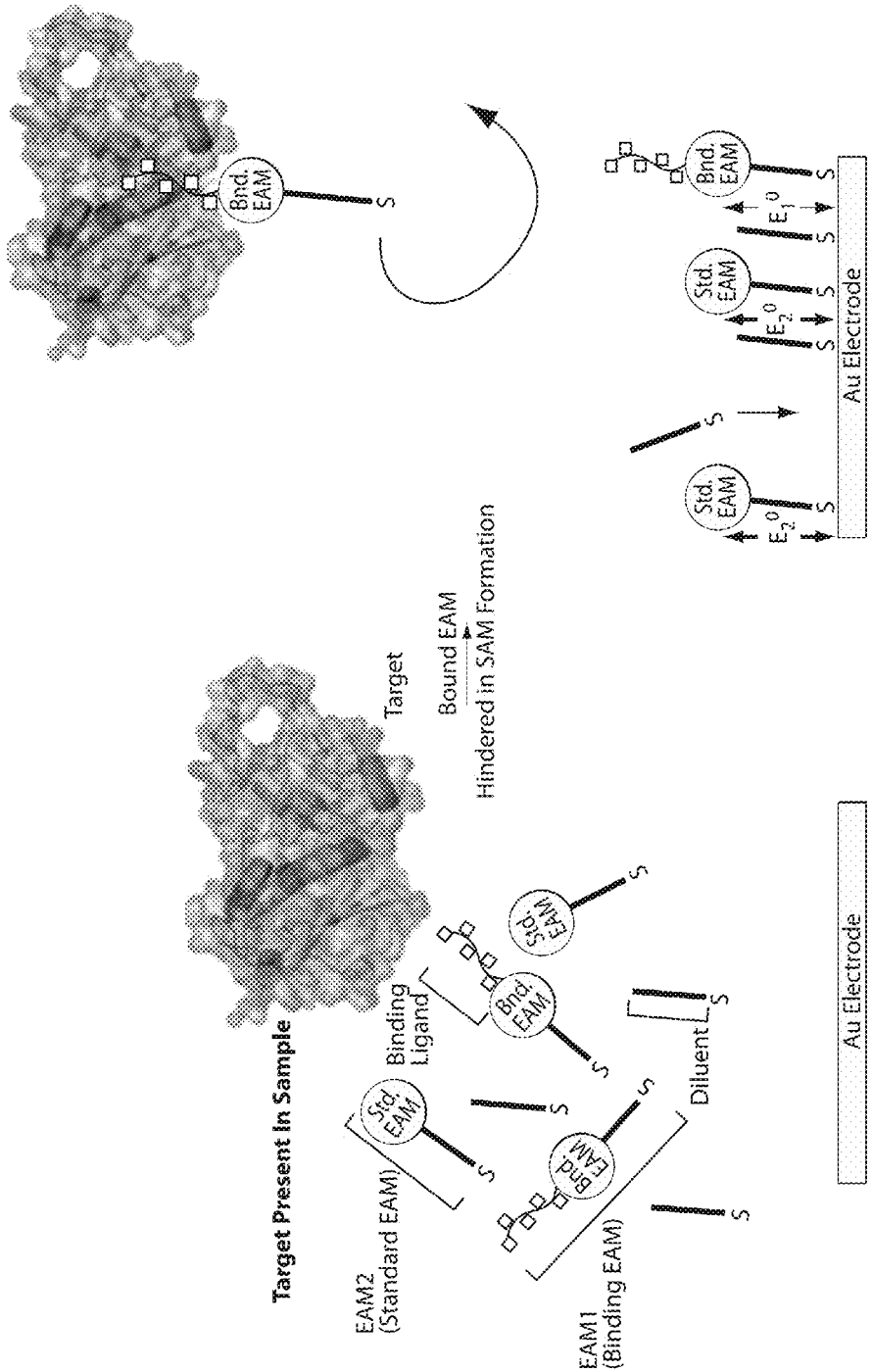
Figure 2:
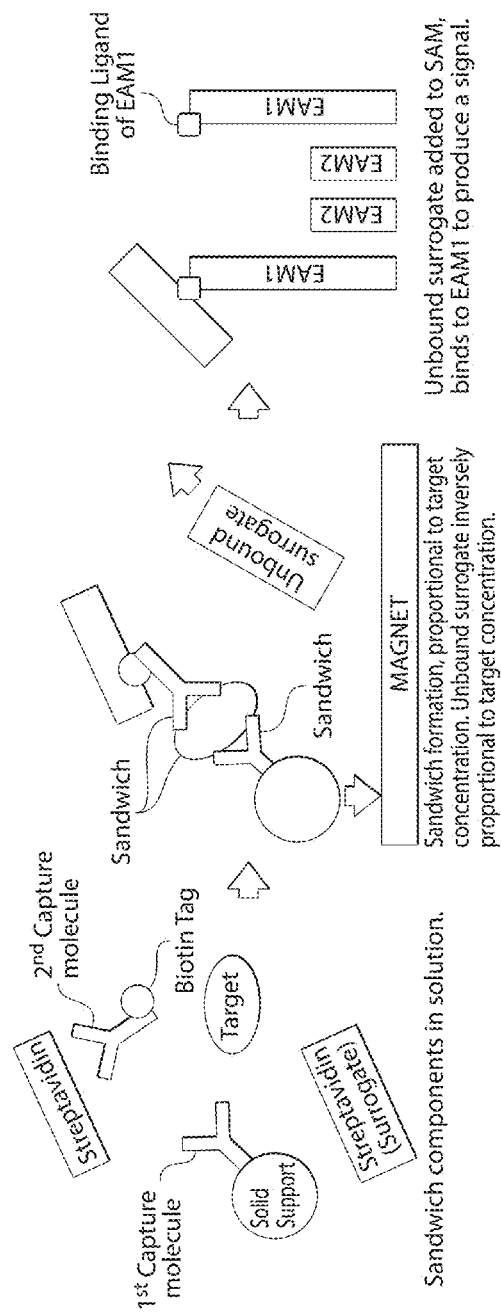
FIG. 2. A schematic describing a method for using a surrogate target for inverse bioelectronic binding assay in solution using peak profiling, according to certain embodiments. Target is first mixed with a capture molecule (e.g. capture antibody) attached to a solid support (e.g. metallic beads), detection molecule (e.g. detection antibody) conjugated with a tag (e.g. biotin tag), and a binding partner of the tag (e.g. streptavidin), and allowed to form a sandwich complex containing beads, capture antibody, target, detection antibody and the binding partner through specific binding. After removal of the sandwich complex (e.g. via a magnet when magnetic beads are used as the solid support), the solution containing unbound binding partner (streptavidin), which serves as a surrogate target, is removed and mixed with EAM1 (binding EAM containing a binding ligand for the surrogate target) and EAM2 (standard EAM). The amount of surrogate target present and available to bind to EAM1 is inversely proportional to the amount of target in the sample. Binding of the surrogate target to EAM1 causes a change in $E_1^0$, resulting in bound EAM1 to exhibit $E_1^{'0}$. The change from $E_1^0$ to $E_1^{'0}$ and $E_1^{'0}$ relative to $E_2^0$ is proportional to the amount of surrogate target and inversely proportional to the amount of target present in a sample. The change is determined through peaking profiling.
Figure 3:
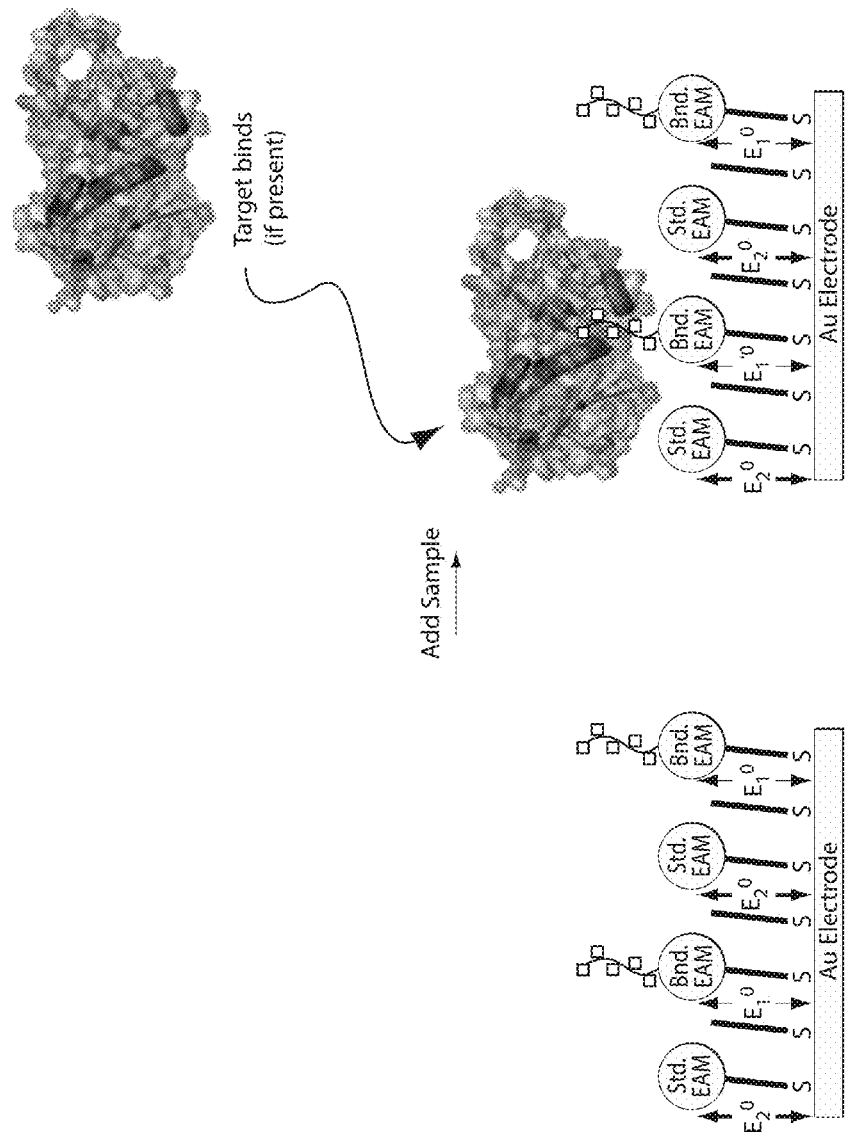
FIG. 3. A schematic describing a method for bioelectronic binding assay on preformed SAM, according to one set of embodiments. Binding of a target to EAM1 (binding EAM containing a binding ligand for said target) causes energy reorganization and affects electron transfer from EAM1 and EAM2, when it is in close vicinity, to the electrode. Binding of the target to EAM1 causes a change in $E_1^0$, resulting in bound EAM1 to exhibit $E_1^{'0}$. The change from $E_1^0$ to $E_1^{'0}$ and $E_1^{'0}$ relative to $E_2^0$ is proportional to the amount of target in the sample. The change can be measured through peak profiling.

In one aspect, a method for detection of a target in a sample based on the change of electrochemical (E-chem) cyclic voltammetry peak profile (CVPP) is provided.

The method may involve at least two or more electroactive moieties (EAMs) comprising a transitional metal complex and an anchor group. Said transitional metal complex may be capable of reversibly or semi-reversibly transferring one or more electrons. Said anchor group may allow said EAMs to covalently attach to a solid support, forming a self-assembled monolayer (SAM) on the surface. Each EAM has a distinct E-chem CVPP $E^0$. In addition, at least one EAM may further comprise a capture ligand that can be recognized and bound by a target or a surrogate target. When a sample is introduced to an EAM either in a solution or on a preformed SAM, the interaction between said capture ligand and said target or surrogate target may lead to change of the properties of the SAM containing all EAMs involved. Said change is reflected in E-chem CVPP and can be detected by an electrochemical detection system. Said E-chem CVPP change is proportional to the amount of said target or surrogate target, can be described in multiple ways, and can be expressed numerically.

With the benefit of having two or more EAMs, each with a distinct E-chem CVPP $E^0$, detection of a target may be exploited in many different ways. Generally, formats for the electronic binding assay can be divided into two major categories: in a solution or on a preformed SAM.

In some embodiments, a sample is introduced to an EAM mix comprising two EAMs, EAM1 with a capture ligand selected to specifically bind to a target of interest and EAM2 without capture ligand, mixed at a certain known ratio in a solution to form an assay mix. Said assay mix comprising said sample and said EAM mix may then be contacted with an electrode and a SAM is allowed to form. In some embodiments, additional binding time can be given before contacting said assay mix with said electrode. If said target of interest is not present in said sample, a SAM may form comprised of both EAM1 and EAM2, proportionally characteristic of said known ratio of said EAM mix. If said target of interest is present in said sample, said target of interest may bind to said capture ligand of EAM1, sterically hindering bound EAM1 from forming a SAM. As a result, the ratio of EAM1 (less) and EAM2 (more) in the final SAM is changed if said target of interest is present. Accordingly a general change of E-chem CVPP involving both $E_1^0$ and $E_2^0$ is detected and is proportional to the amount of said target.

In some embodiments, a sample is added directly to a solution comprising an EAM mix comprising two EAMs, EAM1 and EAM2, mixed at a known ratio, wherein EAM1 further comprises a binding ligand capable of binding to a target of interest, to form an assay mix. If no target is present, EAM1 and EAM2 may form a self-assembled monolayer (SAM) when introduced to an electrode with a particular known ratio of the magnitude of $E_1^0$ and $E_2^0$. If said target of interest is present in said sample, said binding ligand of EAM1 may bind to said target. When bound to said target, said EAM1 is sterically hindered from forming a self-assembled monolayer (SAM). Said assay mix may then be contacted with an electrode. When in contact with said electrode, remaining free EAM1 and EAM2 in said assay mix may self-assemble into a monolayer while the bound EAM1 is hindered from doing so. The ratio of EAM1 and EAM2 in the monolayer varies depending on the amount of EAM1 sterically hindered from forming a SAM due to binding of said target. The magnitude of $E_1^0$ and $E_2^0$ is changed accordingly and is proportional to the amount of target present in said sample.

In some embodiments, a sample is added to a solution for a sandwich immunoassay as further described below, through which a sandwich is formed with the target of interest that is additionally linked to a binding partner. Said binding partner becomes a surrogate target. In some embodiments, an additional washing step may be performed. After removal of unbound surrogate target, the sandwich (containing said linked surrogate target) may be added directly to a solution comprising an EAM mix comprising EAM1 and EAM2, mixed at a known ratio, wherein EAM1 further comprises a binding ligand capable of binding to said surrogate target, to form an assay mix. Said binding ligand of EAM1 may bind to said surrogate target associated with said sandwich; thereby bound EAM1 is sterically hindered from forming a self-assembled monolayer (SAM). When said assay mix is contacted with an electrode, remaining free EAM1 and EAM2 may self-assemble to form a monolayer. The ratio of EAM1 and EAM2 in the monolayer varies depending on the amount of EAM1 sterically hindered from forming a SAM due to the binding of said surrogate target associated with said sandwich. The magnitude of $E_1^0$ and $E_2^0$ is changed accordingly and is proportional to the amount of target present in said sample.

In some embodiments, a sample is added to a solution for a sandwich immunoassay as further described below, through which a sandwich is formed with the target of interest that is additionally linked to a binding partner. After removal of the sandwich, the remaining free binding partners left in solution become a surrogate target that is inversely proportional to the concentration of target of interest present in said sample. The solution containing surrogate targets may be added directly to a solution comprising an EAM mix comprising two EAMs, EAM1 and EAM2, mixed at a known ratio, wherein EAM1 comprises a binding ligand capable of binding said surrogate target, to form an assay mix. When said binding ligand of EAM1 is bound with said surrogate target, EAM1 may be hindered from forming a self-assembled monolayer (SAM). Said assay mix may then be contacted with an electrode, remaining free EAM1 and EAM2 are self-assembled into a monolayer. The ratio of EAM1 and EAM2 in the monolayer varies depending on the amount of EAM1 sterically hindered from forming a SAM due to the binding of said surrogate target in solution. The magnitude of $E_1^0$ and $E_2^0$ is changed accordingly and is proportional to the amount of surrogate target present in solution, which is in turn inversely proportional to the amount of target present in said sample.

In some embodiments, a target of interest in a sample is directly detected using an electrode comprising a preformed SAM comprising multiple EAMs. In some embodiments, said SAM is comprised of EAM1 (with a capture ligand for said target) and EAM2 (without capture ligand) mixed at a known ratio. Binding of said target to said capture ligand of EAM1 may trigger a change in reorganization energy of the EAM1, resulting in a different E-chem CVPP $E_1^{'0}$. Said change may also trigger a general change of E-chem CVPP including $E_1^{'0}$, $E_1^0$ and $E_2^0$ and is proportional to the amount of said target in the sample.

In some embodiments, a target of interest in a sample is indirectly detected through a surrogate target using an electrode comprising a preformed SAM comprising multiple EAMs. In some embodiments, said SAM is comprised of EAM1 (with a capture ligand for surrogate target) and EAM2 (without capture ligand) mixed at a known ratio.

After a standard sandwich immunoassay as further described below, a sandwich complex containing said target that is bound with a binding partner may be formed. In some embodiments, said sandwich complex is isolated and separated from any unbound sandwich assay components, including unbound binding partner. In some embodiments, washing steps can be performed to ensure all unbound binding partner has been removed. After removal of unbound binding partner, said sandwich complex containing said bound binding partner becomes a surrogate target that is proportional to said target. Through recognition between said surrogate target and the capture ligand on EAM1, said sandwich complex may bind to EAM1, changing the reorganization energy of EAM1. In turn, $E_1^0$ is changed to $E_1^{'0}$. The overall change of E-chem CVPP including $E_1^{'0}$, $E_1^0$ and $E_2^0$ is proportional to the amount of said surrogate target bound to said sandwich complex, which is in turn inversely proportional to the amount of target in the sample.

In some embodiments, a target of interest in a sample is indirectly detected through a surrogate target using an electrode comprising a preformed SAM comprising multiple EAMs. In some embodiments, said SAM is comprised of EAM1 (with a capture ligand for surrogate target) and EAM2 (without capture ligand). After a standard sandwich immunoassay, a sandwich containing said target that is bound with a binding partner may be formed. After removal of the sandwich, solution containing remaining unbound binding partner, which becomes a surrogate target that is inversely proportional to said target, is contacted with said electrode. Surrogate target may bind to EAM1, changing the reorganization energy of $EAM_1$. In turn, $E_1^0$ is changed to $E_1^{'0}$. The overall change of E-chem CVPP including $E_1^{'0}$, $E_1^0$ and $E_2^0$ is proportional to the amount of said surrogate target; but inversely proportional to said target in the sample.

In some embodiments, a target of interest in a sample is detected using a preformed SAMs of EAM1 and EAM2 mixed at a known ratio. When a target binds to EAM1, said target may change reorganization energy around EAM1, resulting in $E_1^{'0}$. The change from $E_1^0$ to $E_1^{'0}$ and $E_1^{'0}$ relative to $E_2^0$ is proportional to the amount of target.

As will be appreciated by those in the art, said method has multiple advantages, including, but not limited to 1) better assay quality control with a second EAM as a reference; 2) versatile assay formats, in solution or on a preformed SAM; 3) direct or indirect quantification of a target through a surrogate target, which allows one to use one EAM species to detect many different targets; 4) flexible for detection of a target with or without prior sandwich immunoassay.

Sandwich Immunoassay

By "sandwich immunoassay" and other grammatical equivalents herein has its ordinary meaning in the art and may refer to the process of binding a target of interest between two independent binding ligands. In some embodiments, the components of the sandwich immunoassay are added sequentially. In some embodiments, washing steps may be performed between adding components of the sandwich immunoassay. As will be appreciated by those skilled in the art, antibodies, antibody fragments, find particular use as binding ligands, though many other suitable binding ligands may be used as is further described later.

As will be appreciated by those in the art, a brief description of a sandwich immunoassay on a solid support is provided herein.

A solid support, e.g., magnetic beads, may be modified with a first capture molecule or first capture ligand. This capture molecule, e.g., antibody, binds selectively to a target of interest. As will be appreciated by those in the art, many suitable capture molecules exist and may be chosen based on compatibility with target of interest.

When a sample containing a target of interest is introduced to the solid support with first capture molecule, the target may be found and bound to the first capture molecule or first capture ligand.

A second capture molecule, second capture ligand, detection molecule or detection ligand, such as an antibody conjugated with a tag, is then added to the target-solid support-capture ligand solution. Suitable tags include, but are not limited to, small molecules, e.g., biotin, or enzymes. The detection molecule or detection ligand can bind to the target, leading the formation of a "sandwich" with the target in the middle between the first capture ligand and the second detection ligand. Depending on the nature of the tag, the sandwich containing the target can be quantified with an electrochemical, fluorescent, or optical detection method. In some embodiments, a second capture molecules conjugated with a tag that binds to a binding partner may be used, specifically when said binding partner can also bind to an EAM containing a capture ligand specific for said binding partner, thus making said binding partner suitable for use as a surrogate target.

As will be appreciated by those in the art, the compositions of the invention can be made in a variety of ways, examples of which are outlined below and in U.S. Pat. No. 8,734,631, US20110033869, US20140027309, U.S. patent application Ser. No. 12/253,828, filed Oct. 17, 2008; U.S. patent application Ser. No. 12/253,875, filed Oct. 17, 2008; U.S. Provisional Patent Application No. 61/347,121, filed May 21, 2010; U.S. Provisional Patent Application No. 61/366,013, filed Jul. 20, 2010, U.S. patent application Ser. No. 13/667,713, filed Nov. 2, 2012. In some embodiments, the composition is made according to methods disclosed in U.S. Pat. Nos. 6,013,459, 6,248,229, 7,018,523, 7,267, 939, U.S. patent application Ser. Nos. 09/096,593 and 60/980,733, and U.S. Provisional Application No. 61/087, 102, filed on Aug. 7, 2008, each of which is incorporated herein by reference in its entirety. All patent applications and patents incorporated herein by reference are incorporated by reference in their entirety. In case of conflict, the present specification, including definitions, will control.

Architecture of Electroactive Moieties (EAM)

In general, the architecture of an EAM can be described as follows: an EAM comprises a redox active molecule, generally comprising a transition metal and at least one ligand that provides coordination atoms for the transition metal. Said EAM may be able to covalently attach to the surface of an electrode, generally through a linker. In the spatial vicinity of the redox active molecule, a capture ligand may also be attached, generally in one of two ways, as described herein, and with or without a linker. Binding of the target to the capture ligand results in a change in the electrochemical potential of the redox active molecule, which can then detected and measured in a variety of ways as described herein.

$$\text{AG-Spacer-EAM-(Linker)}_n\text{-CL} \qquad (I)$$

wherein AG is an anchor group, EAM is an electroactive moiety comprising a redox complex, CL is a capture ligand, Spacer is a SAM forming species described herein, and Linker provides space between EAM and CL, with n=0 or 1.

In one embodiment, the coordination atoms for the transition metal of the EAM is provided by the capture ligand, forming a "redox active moiety complex", or ReAMC. In this embodiment, the coordination atom can be part of the capture ligand (e.g. if the capture ligand is a peptide, an amino group can provide the coordination atom) or part of a linker used to attach the capture ligand (e.g. a pyridine linker, etc.).

In another embodiment, ReAMC is a single species, but the capture ligand does not provide a coordination atom; rather, it is spatially close but distinct from the EAM of the ReAMC.

The second EAM, e.g. standard EAM is similar to aforementioned EAM but with no capture ligand.

$$AG\text{-}Spacer\text{-}EAM \qquad (II)$$

wherein AG is an anchor group, EAM is an electroactive moiety comprising a redox complex, Spacer is a SAM forming species described herein.

Electroactive Moieties (EAM)

By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention in some embodiments. In some embodiments, metals that do not change the number of coordination sites upon a change in oxidation state are used, including ruthenium, osmium, iron, platinium and palladium, with osmium, ruthenium. In certain embodiments, iron and/or osmium is used. In some embodiments, one or more EAM (e.g., EAM 1 and EAM 2) does not comprise iron. In some embodiments, ferrocenes and disubstituted ferrocenes are used. Generally, transition metals are depicted herein as TM or M.

The transitional metal and the coordinating ligands form a metal complex. By "ligand" or "coordinating ligand" herein is meant an atom, ion, molecule, or functional group that generally donates one or more of its electrons through a coordinate covalent bond to, or shares its electrons through a covalent bond with, one or more central atoms or ions.

The other coordination sites of the metal are used for attachment of the transition metal complex to either a capture ligand (directly or indirectly using a linker), or to the electrode (frequently using a spacer, as is more fully described below), or both. Thus for example, when the transition metal complex is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the transition metal complex to the electrode. For example, when the transition metal complex is attached to the electrode separately from the binding ligand as is more fully described below, all of the coordination sites of the metal (n) except 1 (n−1) may contain polar ligands.

Suitable small polar ligands, generally depicted herein as "L", fall into two general categories. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". In some instances, ligands that form dipoles are used, since this can contribute to a high solvent reorganization energy.

Some of the structures of transitional metal complexes are shown below:

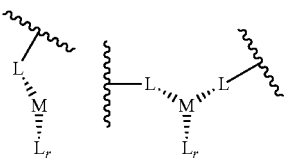

L are the co-ligands that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r may be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r may be zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, cyano (C≡N), $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), which is incorporated by reference in its entirety.

As will be appreciated in the art, any ligand donor(1)-bridge-donor(2) where donor (1) binds to the metal and donor(2) is available for interaction with the surrounding medium (solvent, protein, etc.) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N=C=O), thiocyanates, isonitrile, $N_2$, $O_2$, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has advantages over the others in some embodiments because it is more inert, easier to prepare, and has a more favorable reduction potential. Generally a larger CN/L ratio will give larger shifts.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands can be attached in such a manner as to allow the heteroatoms to serve as coordination atoms.

In some embodiments, organometallic ligands are used. In addition to purely organic compounds for use as redox moieties, and various transition metal coordination complexes with 6-bonded organic ligand with donor atoms as heterocyclic or exocyclic substituents, there is available a wide variety of transition metal organometallic compounds with pi-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, which is incorporated by reference). Such organometallic ligands include cyclic aromatic compounds such as the cyclopentadienide ion [$C_5H_5$ (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference in its entirety. Of these, ferrocene [$(C_5H_5)_2Fe$] and its derivatives are prototypical examples which have been used in a wide variety of chemical (Connelly et al., Chem. Rev. 96:877-910 (1996), incorporated by reference in its entirety) and electrochemical (Geiger et al., Advances in Organometallic Chemistry 23:1-93; and Geiger et al., Advances in Organometallic Chemistry 24:87, incorporated by reference in its entirety) electron transfer or "redox" reactions. Metallocene derivatives of a variety of the first, second and third row transition metals are potential candidates as redox moieties can be covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene) chromium is a prototypical example. Other acyclic π-bonded ligands such as the allyl(−1) ion, or butadiene yield potentially suitable organometallic compounds, and all such ligands, in conduction with other pi-bonded and delta-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand can be generally attached via one of the carbon atoms of the organometallic ligand, although attachment may be via other atoms for heterocyclic ligands. Organometallic ligands include metallocene ligands, including substituted derivatives and the metalloceneophanes (see page 1174 of Cotton and Wilkenson, supra). For example, derivatives of metallocene ligands such as methylcyclopentadienyl or a ligand with multiple methyl groups (e.g., pentamethylcyclopentadienyl), can be used to increase the stability of the metallocene. In one embodiment, only one of the two metallocene ligands of a metallocene are derivatized.

As described herein, any combination of ligands may be used. In some embodiments, the combinations may include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

In general, EAM comprising non-macrocyclic chelators can be bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocylic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g. at least one cyano ligand), bi-dentate, tri-dentate, and polydentate ligands (till to saturate) can be used in the construction of EAMs Generally, it is the composition or characteristics of the ligands that determine whether a transition metal complex is solvent accessible. "Solvent accessible transition metal complex" or grammatical equivalents has its ordinary meaning in the art and may, e.g., refer to a transition metal complex that has at least one (e.g., two, three, four or more) small polar ligands. The actual number of polar ligands will depend on the coordination number (n) of the metal ion. In some embodiments, numbers of polar ligands are (n–1) and (n–2). For example, for hexacoordinate metals, such as Fe, Ru, and Os, solvent accessible transition metal complexes may have one to five small polar ligands (e.g., two to five polar ligands, three to five polar ligands), depending on the requirement for the other sites. Tetracoordinate metals such as Pt and Pd may have one, two or three small polar ligands.

It should be understood that "solvent accessible" and "solvent inhibited" are relative terms. That is, at high applied energy, even a solvent accessible transition metal complex may be induced to transfer an electron.

Ferrocene-Based EAMs

In some embodiments, the EAMs comprise substituted ferrocenes. Ferrocene is air-stable. It can be easily substituted with both capture ligand and anchoring group. Upon binding of the target protein to the capture ligand on the ferrocene, which will not only change the environment around the ferrocene, but also prevent the cyclopentadienyl rings from spinning, the energy may change by approximately 4 kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, each of which is incorporated by reference in their entirety.

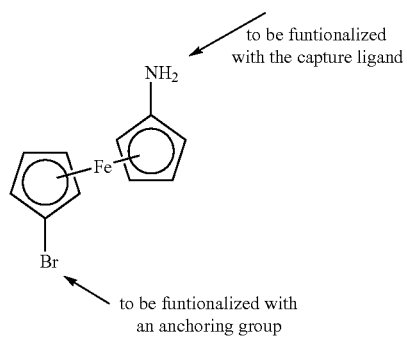

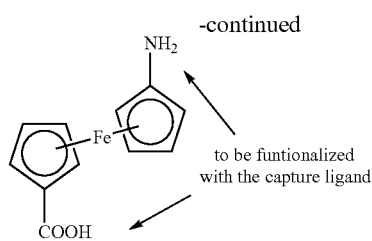

In some embodiments the anchor and capture ligands are attached to the same ligand for easier synthesis. In some embodiments the anchor and capture ligand are attached to different ligands.

There are many ligands that can be used to build the new architecture disclosed herein. They include but not limited to carboxylate, amine, thiolate, phosphine, imidazole, pyridine, bipyridine, terpyridine, tacn (1,4,7-Triazacyclononane), salen (N,N'-bis(salicylidene)ethylenediamine), acacen (N,N'-Ethylenebis(acetylacetoniminate(-)), EDTA (ethylenediamine tetraacetic acid), DTPA (diethylene triamine pentaacetic acid), Cp (cyclopentadienyl), pincer ligands, and scorpionates. In some embodiments, the ligand is pentaamine.

Pincer ligands are a specific type of chelating ligand. A pincer ligand wraps itself around the metal center to create bonds on opposite sides of the metal as well as one in between. The effects of pincer ligand chemistry on the metal core electrons is similar to amines, phosphines, and mixed donor ligands. This creates a unique chemical situation where the activity of the metal can be tailored. For example, since there is such a high demand on the sterics of the complex in order to accommodate a pincer ligand, the reactions that the metal can participate in is limited and selective.

Scorpionate ligand refers to a tridentate ligand which can bind to a metal in a fac manner. The most popular class of scorpionates are the tris(pyrazolyl)hydroborates or Tp ligands. A Cp ligand is isolobal to Tp.

In some embodiments, the following restraints are desirable: the metal complex should have small polar ligands that allow close contact with the solvent.

Spacer Groups

In some embodiments, the EAM or ReAMC is covalently attached to the anchor group (which is attached to the electrode) via an attachment linker or spacer ("Spacer 1"), that further generally includes a functional moiety that allows the association of the attachment linker to the electrode. See for example U.S. Pat. No. 7,384,749, incorporated herein by reference in its entirety and specifically for the discussion of attachment linkers. It should be noted in the case of a gold electrode, a sulfur atom can be used as the functional group (this attachment is considered covalent for the purposes of this invention). By "spacer" or "attachment linker" herein is meant a moiety which holds the redox active complex off the surface of the electrode. In some embodiments, the spacer is a conductive oligomer as outlined herein, although suitable spacer moieties include passivation agents and insulators as outlined below. In some cases, the spacer molecules are SAM forming species. The spacer moieties may be substantially non-conductive. In certain embodiments, the electron coupling between the redox active molecule and the electrode ($H_{AB}$) does not limit the rate in electron transfer.

In addition, attachment linkers can be used between the coordination atom of the capture ligand and the capture ligand itself, in the case when ReAMCs are utilized. Similarly, attachment linkers can be branched. In addition, attachment linkers can be used to attach capture ligands to the electrode when they are not associated in a ReAMC.

One end of the attachment linker may be linked to the EAM/ReAMC/capture ligand, and the other end (although as will be appreciated by those in the art, it need not be the exact terminus for either) may be attached to the electrode.

The covalent attachment of the conductive oligomer containing the redox active molecule (and the attachment of other spacer molecules) may be accomplished in a variety of ways, depending on the electrode and the conductive oligomer used. See for example Structures 12-19 and the accompanying text in U.S. Patent Publication No. 20020009810, hereby incorporated by reference in its entirety.

In general, the length of the spacer is as outlined for conductive polymers and passivation agents in U.S. Pat. Nos. 6,013,459, 6,013,170, and 6,248,229, as well as U.S. Pat. No. 7,384,749 all of which are incorporated by reference in their entireties. As will be appreciated by those in the art, if the spacer becomes too long, the electronic coupling between the redox active molecule and the electrode may decrease rapidly.

Capture Ligands

A variety of molecules can be used in the present invention as capture ligands. By "capture ligand" or "binding ligand" "capture molecule" or "capture binding ligand" or "capture binding species" or "capture probe" or "detection ligand" or "detection molecule" or grammatical equivalents herein is meant a compound that is used to probe for the presence of the target, meaning that it recognizes the target and will bind to it. As is more fully outlined below, attachment of the target to the capture probe may be direct (i.e. the target binds to the capture ligand) or indirect (e.g., one or more capture extender ligands are used). By "covalently attached" herein is meant that two moieties are attached by at least one bond, including sigma bonds, pi bonds and coordination bonds.

In some embodiments, the binding is specific, and the capture ligand is part of a binding pair. By "specifically bind" herein is meant that the ligand binds the target, with specificity sufficient to differentiate between the target and other components or contaminants of the test sample. However, as will be appreciated by those in the art, it is possible to detect target using binding which is not highly specific; for example, the systems may use different capture ligands, for example an array of different ligands, and detection of any particular target is via its "signature" of binding to a panel of binding ligands, similar to the manner in which "electronic noses" work. This may find particular utility in the detection of chemical analytes. The binding should be sufficient to remain bound under the conditions of the assay, including wash steps to remove non-specific binding. This binding can be sufficient to remain bound under the conditions of the assay, including wash steps to remove non-specific binding. Generally, the disassociation constants of the target to the binding ligand will be in the range of at least $10^{-4}$-$10^{-6}$ $M^{-1}$ (e.g., range of $10^{-5}$ to $10^{-9}$ $M^{-1}$, range of $10^{-7}$-$10^{-9}$ $M^{-1}$).

As will be appreciated by those in the art, the composition of the capture ligand will depend on the composition of the target. Capture ligands to a wide variety of targets are known or can be readily found using known techniques. For example, when the target is a single-stranded nucleic acid, the capture ligand may be a complementary nucleic acid. Similarly, the target may be a nucleic acid binding protein and the capture binding ligand is either single-stranded or double stranded nucleic acid; alternatively, the binding ligand may be a nucleic acid-binding protein when the target is a single or double-stranded nucleic acid. When the target is a protein, the binding ligands include proteins or small molecules. As will be appreciated by those in the art, any two molecules that will associate may be used, either as a target or as the binding ligand. Suitable target/binding ligand pairs include, but are not limited to, antibodies/antigens, receptors/ligands, proteins/nucleic acid, enzymes/substrates and/or inhibitors, carbohydrates (including glycoproteins and glycolipids)/lectins, proteins/proteins, proteins/small molecules; and carbohydrates and their binding partners are also suitable target-binding ligand pairs. These may be wild-type or derivative sequences. In one embodiment, the binding ligands are portions (e.g., the extracellular portions) of cell surface receptors that are known to multimerize, such as the growth hormone receptor, glucose transporters (particularly GLUT 4 receptor), transferrin receptor, epidermal growth factor receptor, low density lipoprotein receptor, high density lipoprotein receptor, epidermal growth factor receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor, PDGF receptor, EPO receptor, TPO receptor, ciliary neurotrophic factor receptor, prolactin receptor, and T-cell receptors.

As described herein, the capture ligand can be attached to the coordinating ligand and/or anchor via a covalent bond. The method of attachment of the capture binding ligand can be generally be done as is known in the art, and will depend on the composition of the attachment linker and the capture binding ligand. In general, the capture ligands are attached to the attachment linker through the use of functional groups on each that can then be used for attachment. In some embodiments, functional groups for attachment are amino groups, carboxy groups, oxo groups and thiol groups. These functional groups can then be attached, either directly or through the use of a linker, sometimes depicted herein as "Z". Linkers are known in the art; for example, homo- or hetero-bifunctional linkers as are well known (see 1994 Pierce Chemical Company catalog, technical section on cross-linkers, pages 155-200, incorporated herein by reference). Z linkers include, but are not limited to, alkyl groups (including substituted alkyl groups and alkyl groups containing heteroatom moieties). In some embodiments, the Z linker may be short alkyl groups, esters, amide, amine, epoxy groups and ethylene glycol and derivatives. Z may also be a sulfone group, forming sulfonamide.

In this way, capture binding ligands comprising proteins, lectins, nucleic acids, small organic molecules, carbohydrates, etc. can be added.

In some embodiment, antibodies or a fragment thereof are used as capture ligands. "Antibody" has its ordinary meaning in the art and may refer to, e.g., a member of a family of glycosylated proteins called immunoglobulins, which can specifically combine with an antigen. The term "antibody" includes full-length as well as antibody fragments, as are known in the art, including Fab, Fab2, single chain antibodies (Fv for example), chimeric antibodies, humanized and human antibodies, etc., either produced by the modification of whole antibodies or those synthesized de novo using recombinant DNA technologies, and derivatives thereof.

In some embodiments, whole antibodies are not used. In such cases, this is because antibodies could be too bulky, leading to interference with transducer. Thus in some embodiments, antibody fragments and mimitopes are used as capture ligands.

By "mimitopes" or "mimotope" herein is meant a peptide which has the spatial structure of a biologically important site, e.g., an epitope, or an enzyme active site, or a receptor binding site.

By "epitope" herein is meant the actual site of antibody recognition of the antigen. The term is also used interchangeably with "antigenic determinant" or "antigenic determinant site".

In some embodiments, the capture ligand comprises antibody alternatives, including but not limited to avimer. By "avimer" herein is meant proteins that are evolved from a large family of human extracellular receptor domains by in vitro exon shuffling and phage display. It is generally a multidomain protein with binding and inhibitory properties. See Silverman et al., Nature Biotechnology 23:1556-1561 (2005), herein incorporated by reference.

In some embodiments, the capture ligand comprises oligomeric peptides. These peptides can be obtained using techniques known in the art, including but not limited to phage display, Sidhu et al., Methods Enzymol., 328, 333-363 (2000), and one bead one peptide. For example, the peptide can be obtained using Biopanning. Giodano et al., Nat Med. 7:1249-53 (2001); herein incorporated by reference.

The capture ligand may be nucleic acid, when the target analyte is a nucleic acid or nucleic acid binding proteins; alternatively, as is generally described in U.S. Pat. Nos. 5,270,163, 5,475,096, 5,567,588, 5,595,877, 5,637,459, 5,683,867, 5,705,337, and related patents, all of which are incorporated by reference, nucleic acid "aptamers" can be developed for binding to virtually any target analyte. Similarly, there is a wide body of literature relating to the development of binding partners based on combinatorial chemistry methods. In this embodiment, when the capture ligand is a nucleic acid, exemplary compositions and techniques are outlined in PCT US97/20014, which is incorporated by reference.

In some embodiments, the capture ligand comprises an aptamer. By "aptamer" herein is meant a single-stranded, partially single-stranded, partially double-stranded or double-stranded nucleotide sequence, advantageously a replicatable nucleotide sequence, capable of specifically recognizing a selected nonoligonucleotide molecule or group of molecules by a mechanism other than Watson-Crick base pairing or triplex formation. Aptamers disclosed herein include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Aptamers of the invention include partially and fully single-stranded and double-stranded nucleotide molecules and sequences, synthetic RNA, DNA and chimeric nucleotides, hybrids, duplexes, heteroduplexes, and any ribonucleotide, deoxyribonucleotide or chimeric counterpart thereof and/or corresponding complementary sequence, promoter or primer-annealing sequence needed to amplify, transcribe or replicate all or part of the aptamer molecule or sequence. Aptamers can specifically bind to soluble, insoluble or immobilized selected molecules (e.g., ligands, receptors and effector molecules). Alternatively, the term "aptamer" includes nucleotides capable of shape-specific recognition of chemically bland surfaces by a mechanism distinctly different from specific binding. Aptamers of the instant invention may be selected to specifically recognize a structural shape or surface feature comprising a chemically bland surface (e.g., a silicon chip or carbon nanostructure) rather than the chemical identity of a selected target molecule (e.g., a ligand or receptor). An aptamer may be a molecule unto itself or a sequence segment comprising a nucleotide molecule or group of molecules, e.g., a defined sequence segment or aptameric sequence comprising a synthetic heteropolymer, multivalent heteropolymeric hybrid structure or aptameric multimolecular device.

Self-Assembled Monolayer (SAM)

EAMs used in this invention may have the spacer and anchor capable of forming a self-assembled monolayer on an electrode. By "monolayer" or "self-assembled monolayer" or "SAM" or grammatical equivalents herein is meant a relatively ordered assembly of molecules spontaneously chemisorbed on a surface, in which the molecules are oriented approximately parallel to each other and roughly perpendicular to the surface. At least a portion (e.g., each) of the molecules may include a functional group that adheres to the surface, and a portion that interacts with neighboring molecules in the monolayer to form the relatively ordered array. A "mixed" monolayer comprises heterogeneous spacers, that is, where at least two different molecules make up the monolayer. As outlined herein, the use of a monolayer may reduce the amount of non-specific binding of biomolecules to the surface, and, in the case of nucleic acids, may increase the efficiency of oligonucleotide hybridization as a result of the distance of the oligonucleotide from the electrode. Thus, a monolayer may facilitate the maintenance of the target enzyme away from the electrode surface. In addition, a monolayer may serve to keep charge carriers away from the surface of the electrode. Thus, this layer may help to prevent electrical contact between the electrodes and the ReAMs, or between the electrode and charged species within the solvent. Such contact can result in a direct "short circuit" or an indirect short circuit via charged species which may be present in the sample. Accordingly, the monolayer may be tightly packed in a uniform layer on the electrode surface, such that a minimum of "holes" exist. The monolayer thus may also serve as a physical barrier to block solvent accessibility to the electrode.

In some embodiments, the monolayer may be made up of multiple species or types of EAM molecules, in addition to non-electroactive diluent molecules.

By "species of EAM" or "type of EAM" or grammatical equivalents herein is meant a distinct EAM having a particular structure and $E^o$. Many copies of this molecule may be present, and are considered to be the same species of EAM (e.g. EAM1).

In some embodiments, the spacer enabling the formation of SAM comprises conductive oligomers. By "conductive oligomer" herein is meant a substantially conducting oligomer (e.g., a linear substantially conducting oligomer), some embodiments of which are referred to in the literature as "molecular wires". By "substantially conducting" herein is meant that the oligomer is capable of transfering electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electroactive polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

In addition, the terminus of at least some of the conductive oligomers in the monolayer may be electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in one embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target is nucleic acid such as DNA or RNA, the nucleic acid is repelled or prevented from lying down on the surface, to facilitate hybridization. Terminal groups may include —NH, —OH, —COOH, and alkyl groups such as —CH$_3$, and (poly)alkyloxides such as (poly)ethylene glycol. In some embodiments, a terminal group may be —OCH$_2$CH$_2$OH, —(OCH$_2$CH$_2$O)$_2$H, —(OCH$_2$CH$_2$O)$_3$H, or —(OCH$_2$CH$_2$O)$_4$H.

In one embodiment, it is possible to use mixtures of conductive oligomers with different types of terminal groups. Thus, for example, some of the terminal groups may facilitate detection, and some may prevent non-specific binding.

In some embodiments, the electrode further comprises a passivation agent, e.g., in the form of a monolayer on the electrode surface. For some targets the efficiency of target binding (e.g., hybridization) may increase when the binding ligand is at a distance from the electrode. In addition, the presence of a monolayer can decrease non-specific binding to the surface (which can be further facilitated by the use of a terminal group, outlined herein. A passivation agent layer may facilitate the maintenance of the binding ligand and/or target away from the electrode surface. In addition, a passivation agent may serve to keep charge carriers away from the surface of the electrode. Thus, this layer may help to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents may be tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accessibility to the electrode. As such, the passivation agents themselves may in fact be either (1) conducting or (2) nonconducting, e.g., insulating, molecules. Thus, in one embodiment, the passivation agents are conductive oligomers, as described herein, with or without a terminal group to block or decrease the transfer of charge to the electrode. Other passivation agents which may be conductive include oligomers of —(CF$_2$)$_n$—, —(CHF)$_n$— and —(CFR)$_n$—. In one embodiment, the passivation agents are insulator moieties.

In some embodiments, the monolayers comprise insulators. An "insulator" is a substantially nonconducting oligomer (e.g., linear nonconducting oligomer). By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —(CH2)16 molecules, still may transfer electrons, albeit at a slow rate.

In some embodiments, the insulators have a conductivity, S, of about 10-7 Ω-1 cm-1 or lower (e.g., less than about 10-8 Ω$^{-1}$ cm$^{-1}$). Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow (e.g., substantially inhibit or slow), electron transfer. In some embodiments, the alkyl or heroalkyl chains are from about four to about 18 atoms in length (e.g., from about six to about 16 atoms in length).

The passivation agents, including insulators, may be substituted with R groups as defined herein to alter the packing of the moieties or conductive oligomers on an electrode, the hydrophilicity or hydrophobicity of the insulator, and the flexibility, e.g., the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the target, etc. For example, there may be charged groups on the terminus to form a charged surface to encourage or discourage binding of certain targets or to repel or prevent from lying down on the surface.

The length of the passivation agent may vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, e.g., nitrogen or sulfur (sulfur derivatives may not be used when the electrode is gold). Insulators may be of the form —(CH$^2$)$_n$— having a thiol or disulfide terminus for attachment to gold. Also, the alternate end of the insulator may terminate in a hydrophilic group such as oligoethylene glycol, —OH, or —COOH.

In some embodiments, the electrode is a metal surface and need not necessarily have interconnects or the ability to do electrochemistry.

Anchor Groups

The present invention provides compounds comprising an anchor group. By "anchor" or "anchor group" herein is meant a chemical group that attaches the compounds of the invention to an electrode.

As will be appreciated by those in the art, the composition of the anchor group will vary depending on the composition of the surface to which it is attached. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

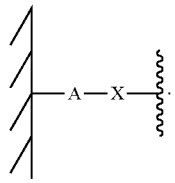

Structure 1

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (e.g., a primary amine; see for example Deinhammer et al., Langmuir 10:1306-1313 (1994)). Thus, A moieties include, but are not limited to, silane moieties, sulfur moieties (including alkyl sulfur moieties), and amino moieties.

Sulfur Anchor Groups

For the clarity of this invention, sulfur anchor groups are described as an example. Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Thus, for example, when the electrode is a gold electrode, and "A" is a sulfur atom or moiety, such as generally depicted below in Structure 6, multiple sulfur atoms may be used to attach the conductive oligomer to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

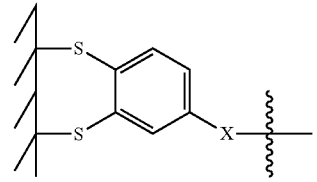

Structure 2

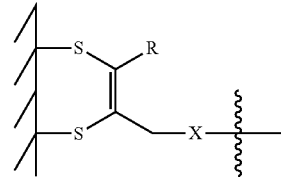

Structure 3

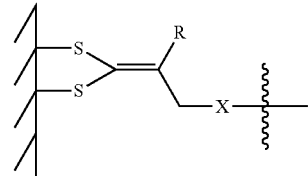

Structure 4

It should also be noted that similar to Structure 4, it may be possible to have a conductive oligomer terminating in a single carbon atom with three sulfur moieties attached to the electrode.

The anchors can be synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

Electrodes

By "electrode" herein is meant a composition, which, when connected to an electronic device, is able to sense a current or charge and convert it to a signal. Electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide (Mo$_2$O$_6$), tungsten oxide (WO$_3$) and ruthenium oxides; and carbon (including glassy carbon electrodes, graphite and carbon paste). In some embodiments, the electrodes may include gold, silicon, carbon, and metal oxide electrodes. In some instances, the electrode includes gold.

The electrodes described herein are depicted as a flat surface, which is only one of the possible conformations of the electrode and is for schematic purposes only. The conformation of the electrode can vary with the detection method used. For example, flat planar electrodes may be used for optical detection methods, or when arrays of nucleic acids are made, thus requiring addressable locations for both synthesis and detection. Alternatively, for single probe analysis, the electrode may be in the form of a tube, with the components of the system such as SAMs, EAMs and capture ligands bound to the inner surface. This can allow a maximum of surface area containing the nucleic acids to be exposed to a small volume of sample.

The electrodes of the invention are generally incorporated into biochip cartridges and can take a wide variety of configurations, and can include working and reference electrodes, interconnects (including "through board" interconnects), and microfluidic components. See for example U.S. Pat. No. 7,312,087, incorporated herein by reference in its entirety.

The biochip cartridges can include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

In a one embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, materials may include printed circuit board materials. Circuit board materials generally are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnectors may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Detection

Electron transfer is generally initiated electronically, e.g., using voltage. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Solid Supports

The target analytes can be detected using solid supports comprising electrodes. In some embodiments, a second solid support independent of the electrode may also be used. By "solid support" or "substrate" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, In some embodiments, printed circuit board (PCB) materials are used. In one embodiment, solid support is selected from microparticles, magnetic microparticles, beads, and microchannels.

Detection

Electron transfer between the redox active molecule and the electrode can be detected in a variety of ways, with electronic detection, including, but not limited to, amperommetry, voltammetry, capacitance and impedance. These methods can include time or frequency dependent methods based on AC or DC currents, pulsed methods, lock in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target.

The device for measuring electron transfer amperometrically involves sensitive current detection and includes a means of controlling the voltage potential, usually but not limited to a potentiostat. This voltage can be optimized with reference to the potential of the redox active molecule.

In some embodiments, alternative electron detection modes are utilized. For example, potentiometric (or voltammetric) measurements involve non faradaic (no net current flow) processes and are utilized traditionally in pH and other ion detectors. Similar sensors can be used to monitor electron transfer between the redox active molecules and the electrode. In addition, other properties of insulators (such as resistance) and of conductors (such as conductivity, impedance, and capicitance) could be used to monitor electron transfer between the redox active molecules and the electrode. Finally, any system that generates a current (such as electron transfer) also generates a small magnetic field, which may be monitored in some embodiments.

In some embodiments, electron transfer is initiated and detected using direct current (DC) techniques. As noted above, the change in the profile of $E^0$ of the redox active molecule before and after binding can allow the detection of the target. As will be appreciated by those in the art, a number of suitable methods may be used to detect the electron transfer.

In some embodiments, electron transfer is initiated using alternating current (AC) methods. A first input electrical signal is applied to the system, e.g., via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in some embodiments of the present methods, the AC amplitude ranges from about 1 mV to about 1.1 V (e.g., from about 10 mV to about 800 mV, from about 10 mV to about 500 mV). The AC frequency can range from about 0.01 Hz to about 10 MHz (e.g., from about 1 Hz to about 1 MHz, from about 1 Hz to about 100 kHz).

In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages may be from about 1 V to about +1.1 V (e.g., from about 500 mV to about +800 mV, from about 300 mV to about 500 mV). On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials, can give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity.

In some embodiments, measurements of the system are taken at least two separate amplitudes or overpotentials. In some instances, measurements at a plurality of amplitudes are used. As noted above, changes in response as a result of changes in amplitude may form the basis of identification, calibration and quantification of the system.

In some embodiments, the AC frequency is varied. At different frequencies, different molecules can respond in different ways. As will be appreciated by those in the art, increasing the frequency generally increases the output current. However, when the frequency is greater than the rate at which electrons may travel between the electrode and the redox active molecules, higher frequencies can result in a loss or decrease of output signal. At some point, the frequency can be greater than the rate of electron transfer through even solvent inhibited redox active molecules, and then the output signal can also drop.

In addition, the use of AC techniques can allow the significant reduction of background signals at any single frequency due to entities other than the covalently attached EAMs, i.e. "locking out" or "filtering" unwanted signals. That is, the frequency response of a charge carrier or redox active molecule in solution can be limited by its diffusion coefficient. Accordingly, at high frequencies, a charge carrier may not diffuse rapidly enough to transfer its charge to the electrode, and/or the charge transfer kinetics may not be fast enough. This can be significant in embodiments that do not utilize a passivation layer monolayer or have partial or insufficient monolayers, i.e. where the solvent is accessible to the electrode. However, using the present AC techniques, one or more frequencies can be chosen that prevent a frequency response of one or more charge carriers in solution, whether or not a monolayer is present. This is significant since many biological fluids such as blood contain significant amounts of redox active molecules which can interfere with amperometric detection methods.

In some embodiments, measurements of the system are taken at least two separate frequencies, In some instances, measurements are taken at a plurality of frequencies. A plurality of frequencies includes a scan. In one embodiment, the frequency response is determined at least two (e.g., at least about five, at least about ten frequencies).

Signal Processing

After transmitting the input signal to initiate electron transfer, an output signal is received or detected. The presence and magnitude of the output signal can depend on the overpotential/amplitude of the input signal; the frequency of the input AC signal; the architecture of electroactive moieties; the composition of the intervening medium, i.e. the impedance, between the electron transfer moieties; the DC offset; the environment of the system; and the solvent. At a given input signal, the presence and magnitude of the output signal can depend in general on a change in the oxidation state of the metal ion. Thus, upon transmitting the input signal, comprising an AC component and a DC offset, electrons can be transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current can depend on a number of parameters. By varying these parameters, the system may be optimized in a number of ways.

In general, AC currents generated in the present invention range from about 1 femtoamp to about 1 milliamp (e.g., from about 50 femtoamps to about 100 microamps, from about 1 picoamp to about 1 microamp).

Apparatus

The present invention further provides apparatus for the detection of analytes using AC detection methods. The apparatus can include a test chamber which has at least a first measuring or sample electrode, and a second measuring or counter electrode. Three electrode systems are also useful. The first and second measuring electrodes can be in contact with a test sample receiving region, such that in the presence of a liquid test sample, the two electrodes may be in electrical contact.

In yet another embodiment, the first measuring electrode comprises a redox active complex, covalently attached via a spacer (e.g., via a conductive oligomer), such as those described herein. Alternatively, the first measuring electrode can comprise covalently attached redox active molecules and binding ligands.

The apparatus can further comprise a voltage source electrically connected to the test chamber; that is, to the measuring electrodes. In some embodiments, the voltage source is capable of delivering AC and DC voltages, if needed.

In an embodiment, the apparatus further comprises a processor capable of comparing the input signal and the output signal. The processor can be coupled to the electrodes and configured to receive an output signal, and thus detect the presence of the target.

Samples

The targets are generally present in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, such as mammals (e.g. humans); environmental samples (including, but not limited to, air, agricultural, water and soil samples); plant materials; biological warfare agent samples; research samples, purified samples, raw samples, etc.; as will be appreciated by those in the art, virtually any experimental manipulation may have been done on the sample. Some embodiments utilize target samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Many patient-derived pathological samples are routinely fixed and paraffin-em bedded to allow for histological analysis and subsequent archival storage.

EXAMPLES

Example 1

Figure 4A:
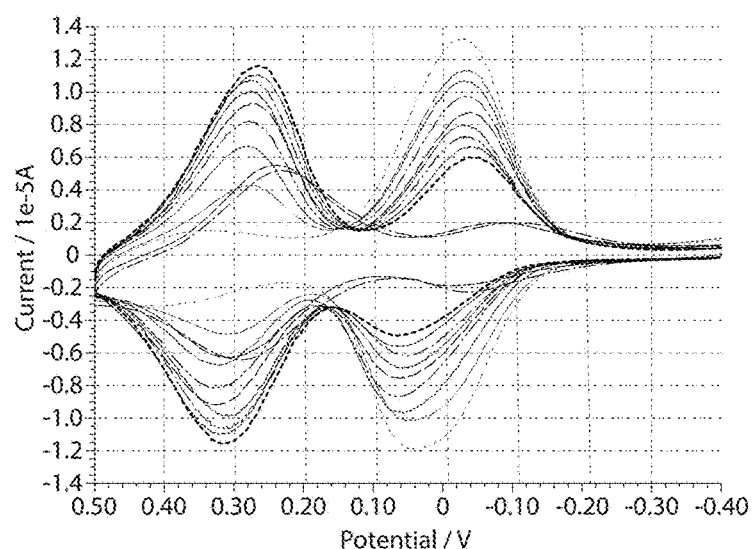
FIGS. 4A to 4B. Data showing the effect of changing ratio of two EAMs in a SAM, according to certain embodiments. When varying concentrations of one EAM (PB65-99) is mixed with a fixed concentration of another EAM (BP65-77) for SAM formation, the CVPP for both EAMs changes (FIG. 4A). The signal determined through peak profiling increases with increasing amount of the EAM (FIG. 4B).
Figure 4B:
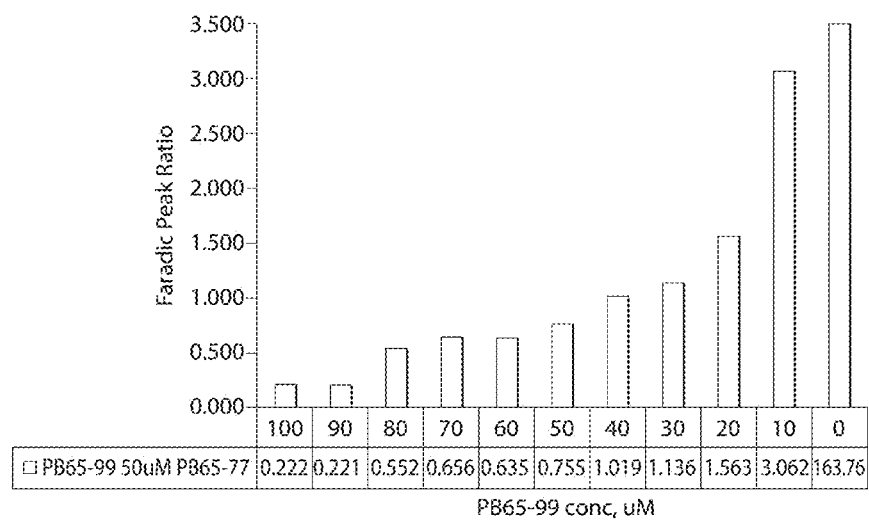
Figure 5A:
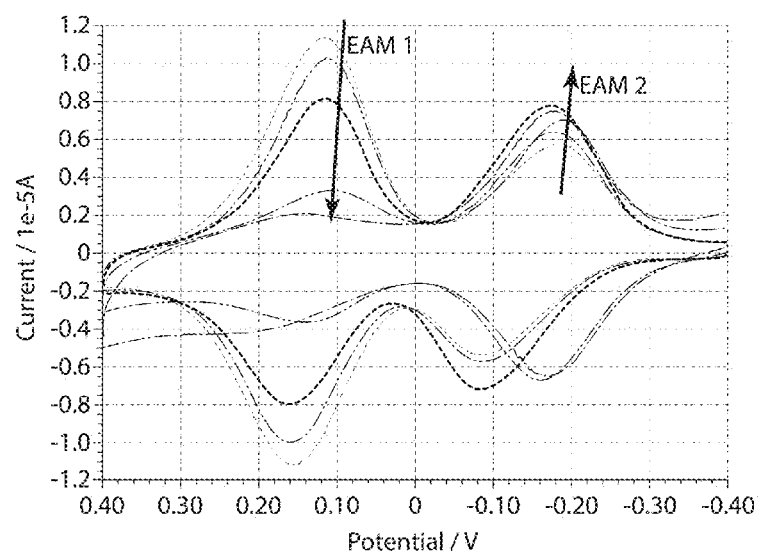
FIGS. 5A to 5B. Data showing dose response of a target with bioelectronic binding assay using peak profiling, according to certain embodiments.
Figure 5B:
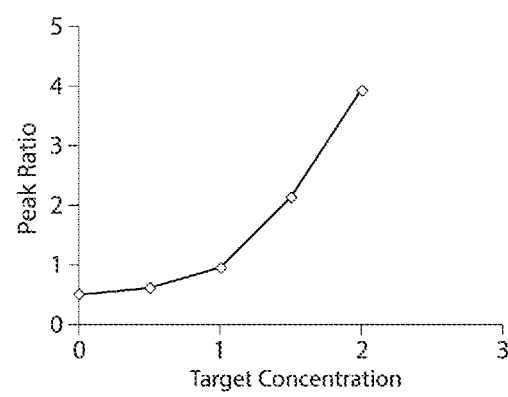

To demonstrate proof-of-concept, varying concentrations (0-100 uM) of EAM1 with biotin as capture ligand (BP65-99, binding EAM) was mixed with 50 uM of EAM2 (BP65-77, standard EAM without capture ligand) to form a series of EAM mix in PBS. After 2 minutes, 40 ul of each said EAM mix series was added to a chip (with multiple virtual wells and a gold electrode at the bottom of each well) and EAMs were allowed to form a SAM for 5 minutes. The chip was washed with test buffer (200 mM LiClO4) twice. After addition of 150 ul of the test buffer, the chip was plugged into the CHI650C system (home-made electrochemical detection system). Currents at a range of voltages were measured and plotted (shown in the left chart of FIG. 4A). In the chart, the CVPP for EAM1 is shown on left and is decreased as the concentration decreases; the CVPP for EAM2 is shown on right and is increased as a result of reduced number of EAM1 in the SAM. The change is quantifiable as shown in the Histogram in FIG. 4B.

Example 2

Figure 6:
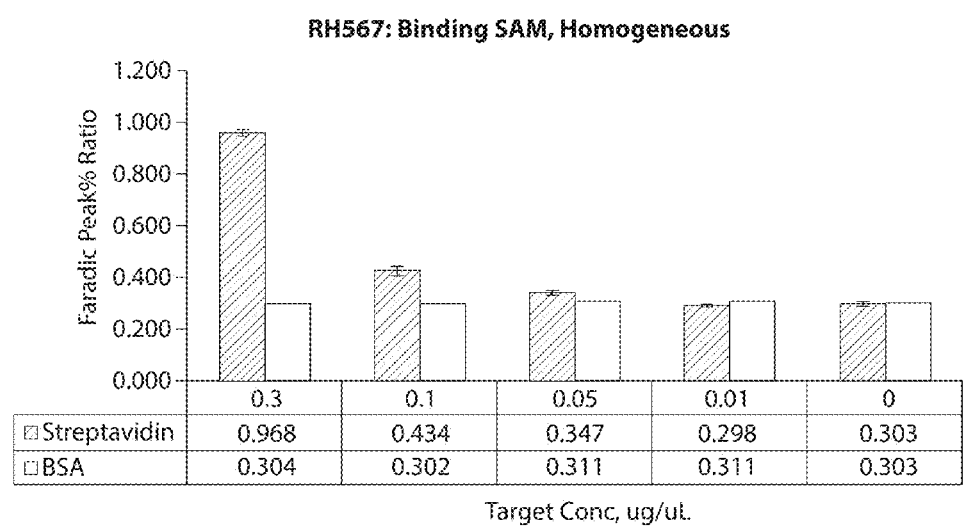
FIG. 6. Data showing the specificity of bioelectronic binding assay using peak profiling, according to certain embodiments. Varying concentrations of a target (e.g., Streptavidin) is mixed with a fixed concentration of a non-target (e.g., BSA) first, and then are introduced to EAM1 (binding EAM with biotin as a capture ligand) and EAM2 (standard EAM without capture ligand). After SAM formation, due to specific binding of Streptavidin to biotin, the dose response is only observed with Streptavidin, but not BSA.

To demonstrate the utility of the bioelectronic binding assay, an experiment with a mock sample containing a target (Streptavidin) and a non-target (BSA) was carried out and is described herein. First, dilutions of Streptavidin and BSA were prepared, both with concentrations of 0.3, 0.1, 0.05, 0.01 and 0 ug/ul. Second, equal ratio of EAM1 (PB65-99, binding EAM with biotin as capture ligand) and EAM2 (PB65-77, standard EAM without capture ligand) were mixed (50 uM each) to form a solution phase EAM mix. Third, 40 ul of said mock sample containing same amount of Streptavidin and BSA was added to 17.15 ul of solution phase EAM mix to form an assay mix and allowed to incubate for 2 minutes. Fourth, 40 ul each of the assay mix was added to chip (chip comprising multiple virtual wells with a gold electrode at the bottom of each well) and EAMs were allowed to form a SAM for 5 minutes. Fifth, the chip was washed with test buffer (200 mM LiClO4) twice. After addition of 150 ul of the test buffer, the chip was plugged into the CHI650C system (home-made electrochemical detection system). CVPPs for EAM1 and EAM2 were measured and peak percentage ratio was calculated. As shown in FIG. 6, signal for Streptavidin decreases with its decreasing concentrations while signal for BSA remains constant regardless of its concentration, suggesting that the observed change in CVPP is caused by specific binding of Streptavidin to biotin contained as the binding ligand of EAM1. In other words, binding of Streptavidin to biotin binding ligand on EAM1 sterically hinders EAM1 from forming SAM, resulting in less EAM1 and more EAM2 in the SAM. The change is quantifiable.

We claim:

1. A method, comprising:
    contacting a sample with a mixture comprising two or more electroactive moieties to form an assay mix, wherein:
    at least two of the two or more electroactive moieties have a different redox potential $E^0$,
    at least two of the two or more electroactive moieties comprise a transitional metal complex and an anchor group, and
    at least one of the two or more electroactive moieties comprises a capture ligand configured to be recognized and bound by a target;
    contacting the assay mix with an electrode under conditions, wherein at least one of the two or more electroactive moieties form a self-assembled monolayer (SAM); and
    detecting a signal to determine an electrochemical cyclic voltammetry peak profile.

2. The method of claim 1, wherein the electrochemical cyclic voltammetry peak profile in the presence of the target is different than the electrochemical cyclic voltammetry peak profile in the absence of the target.

3. The method of claim 1, wherein the electrochemical cyclic voltammetry peak profile is proportional to the amount of said target.

4. The method of claim 1, wherein said target is bound between (i) a first capture molecule bound to a solid support and (ii) a second capture molecule comprising a tag bound to a binding partner, the binding partner being capable of binding to EAM1.

5. The method of claim 1, wherein the target is bound between (i) a first capture molecule bound to a solid support and (ii) a second capture molecule with a tag bound with a binding partner and is removed.

6. The method of claim 1, wherein the transition metal complex includes a transition metal selected from the group consisting of iron, ruthenium, and osmium.

7. The method of claim 1, wherein the transition metal complex comprises a ferrocene or substituted ferrocene.

8. The method of claim 1, wherein the anchor group comprises a sulfur, amine, silicon, pyridinyl, or another group that interacts with an electrode.

9. The method of claim 1, comprising a first electroactive moiety (EAM1) with $E_1^0$ and a second electroactive moiety (EAM2) with $E_2^0$, wherein EAM1 further comprises said capture ligand that can be recognized and bound by the target or a surrogate target.

10. The method of claim 9, wherein the target or the surrogate target is bound to EAM1 through said capture ligand.

11. The method of claim 9, wherein the target or surrogate target, if bound, sterically hinders the EAM1 from forming the SAM.

12. The method of claim 9, wherein the target or surrogate target is bound to EAM1, causing reorganization of energy.

13. A method, comprising:
   contacting a sample with a mixture comprising two or more electroactive moieties to form an assay mix, wherein:
   at least two of the two or more electroactive moieties have a different redox potential $E^0$,
   the two or more electroactive moieties comprise a transitional metal complex and an anchor group, and
   at least one of the two or more electroactive moieties comprises a capture ligand that is capable of binding to a target;
   contacting the assay mix with an electrode under conditions, wherein at least one of the two or more electroactive moieties form a self-assembled monolayer (SAM); and
   detecting a signal to determine an electrochemical cyclic voltammetry peak profile as an indication of the presence of said target in said sample.

14. A method of detecting at least one target analyte in a sample, comprising:
   a) contacting the sample with:
      a first capture ligand comprising a binding site specific for the target,
      a solid support,
      a second capture ligand comprising a binding site specific for the target, being bound in a different location than the first capture ligand,
      a tag on the second capture ligand capable of binding to a binding partner, and
      a binding partner capable of binding to the tag of the second capture ligand and an EAM as a surrogate target to form a sandwich;
   b) isolating the sandwich and unbound binding partners;
   c) contacting the sandwich or the unbound binding partners from step b) with a mixture comprising two or more electroactive moiety species to form an assay mix, wherein:
   at least two of the two or more electroactive moieties have a different redox potential $E^0$,
   the two or more electroactive moieties comprise a transitional metal complex and an anchor group, and
   at least one of the two or more electroactive moieties comprises a capture ligand that is capable of binding to the target or the surrogate tag;
   d) contacting the assay mix with an electrode under conditions wherein EAMs form a self-assembled monolayer (SAM); and
   e) detecting a signal to determine an electrochemical cyclic voltammetry peak profile as an indication of the presence of said target in said sample.

15. The method of any one of claims 1, 13, and 14, wherein the mixture comprises a first electroactive moiety (EAM1) and a second electroactive moiety (EAM2) in a solution, wherein EAM1 comprises a capture ligand that is configured to be bound by that target.

16. The method of claim 15, wherein the target is directly bound to the EAM1 through the capture ligand and wherein at least a portion of the EAM1 bound to the target are not present in the SAM.

17. The method of claim 15, wherein the ratio of EAM1 and EAM2 in the SAM in the presence of the target is different than the electrochemical cyclic voltammetry peak profile in the absence of the target.

18. The method of claim 15, wherein a target is bound to EAM1, causing reorganization of energy; thereby resulting in change of $E_1^0$ to $E_1^{'0}$, which in turn changes CVPP ($E_1^0$, $E_1^{'0}$, and $E_2^0$).

19. A method of detecting at least one target analyte in a sample, said method comprising:
   a) providing a solid support comprising an electrode comprising a pre-formed self-assembled monolayer (SAM) comprising two or more electroactive moiety species, wherein:
   at least two of the two or more electroactive moieties have a different redox potential $E^0$,
   the two or more electroactive moieties comprise a transitional metal complex and an anchor group, and
   at least one of the two or more electroactive moieties comprises a capture ligand that is capable of binding to the target or a surrogate target;
   b) contacting said sample with:
      a first capture ligand comprising a binding site specific for the target,
      a solid support,
      a second capture ligand comprising a binding site specific for the target, being bound in a different location than the first capture ligand,
      a tag on the second capture ligand capable of binding to a binding partner, and
      a binding partner capable of binding to the t of the second capture ligand and an EAM as the surrogate target to form a sandwich;
   c) isolating the sandwich and unbound binding partners;
   d) contacting either said sandwich or said unbound binding partners from step c) with the electrode from step a); and
   e) detecting signal to determine electrochemical (E-chem) cyclic voltammetry peak profile (CVPP) as an indication of the presence of said target in said sample.

20. The method of any one of claims 14, 19, 4 and 5, wherein the capture ligand and capture-molecules are independently selected from the group consisting of monoclonal antibodies, fragments of monoclonal antibodies, polyclonal antibodies, fragments of polyclonal antibodies, proteins, peptides, aptamers, nucleic acids, and small molecules.

21. A method of as in any one of claims 14 and 19, wherein the electrochemical cyclic voltammetry peak profile is proportional to the amount of unbound surrogate target present in the mixture and the amount of surrogate target is inversely proportional to the amount of said target in the sample.

22. A method of detecting at least one target analyte in a sample, said method comprising:

providing a solid support comprising an electrode comprising a pre-formed self-assembled monolayer (SAM) comprising two or more electroactive moiety species, wherein:

at least two of the two or more electroactive moieties have a different redox potential $E^0$, the two or more electroactive moieties comprise a transitional metal complex and an anchor group, and at least one of the two or more electroactive moieties comprises a capture ligand that is capable of binding to the target;

contacting the electrode with the sample; and detecting a signal to determine an electrochemical cyclic voltammetry peak profile as an indication of the presence of said target in said sample.

23. The method of any one of claims 22 and 19, wherein a sample is introduced to a preformed SAM comprising a first electroactive moiety (EAM1) and a second electroactive moiety (EAM2), wherein EAM1 comprises a capture ligand that is configured to be bound by a target or surrogate target.

24. The method of claim 23, wherein a target is bound to EAM1, causing reorganization of energy and thereby resulting in change of $E_1^0$ to $E_1'^0$, which in turn changes CVPP ($E_1^0$, $E_1'^0$, and $E_2^0$).

25. A composition, comprising:

an electrode comprising a self-assembled monolayer (SAM) comprising two or more electroactive moiety species, wherein:

at least two of the two or more electroactive moieties have a different redox potential $E^0$, the two or more electroactive moieties comprise a transitional metal complex and an anchor group, and at least one of the two or more electroactive moieties comprises a capture ligand that is configured to be recognized and bound by the target or surrogate target.

* * * * *